(12) United States Patent
Mohammad (10) Patent No.: US 10,357,333 B2
(45) Date of Patent: Jul. 23, 2019

(54) ENDODONTIC FILE SYSTEM FOR CLEANING AND SHAPING A ROOT CANAL

(71) Applicant: Imam Abdulrahman bin Faisal University, Dammam (SA)

(72) Inventor: Shahnaz Mohammad, Dammam (SA)

(73) Assignee: Imam Abdulrahman bin Faisal University, Dammam (SA)

( * ) Notice: Subject to any disclaimer, the term of this patent is extended or adjusted under 35 U.S.C. 154(b) by 0 days.

(21) Appl. No.: 15/350,167

(22) Filed: Nov. 14, 2016

(65) Prior Publication Data

US 2018/0132972 A1 May 17, 2018

(51) Int. Cl.
*A61C 1/18* (2006.01)
*A61C 5/42* (2017.01)
*A61C 5/44* (2017.01)
*A61C 1/00* (2006.01)

(52) U.S. Cl.
CPC ............ *A61C 1/186* (2013.01); *A61C 5/42* (2017.02); *A61C 5/44* (2017.02); *A61C 1/003* (2013.01)

(58) Field of Classification Search
CPC .......... A61C 5/025; A61C 5/023; A61C 3/02; A61C 1/003; A61C 1/186; A61C 5/42; A61C 5/44
See application file for complete search history.

(56) References Cited

U.S. PATENT DOCUMENTS

| | | | | |
|---|---|---|---|---|
| 238,244 | A * | 3/1881 | Morgan | B23B 39/205 408/117 |
| 1,824,398 | A * | 9/1931 | Fleischhacker | A61C 1/082 433/130 |
| 2,835,035 | A * | 5/1958 | Rauscher | A61C 1/085 433/175 |
| 4,197,645 | A * | 4/1980 | Scheicher | A61B 17/1673 408/42 |
| 4,268,251 | A * | 5/1981 | Takasugi | A61C 5/44 433/102 |
| 4,321,040 | A * | 3/1982 | Miller | A61C 5/48 433/102 |
| 4,536,156 | A | 8/1985 | Cattin | |
| 5,205,682 | A * | 4/1993 | Jinkins | B23B 39/162 408/130 |

(Continued)

OTHER PUBLICATIONS

Özkan Adigüzel, "A Literature Review of Self Adjusting File", International Dental Research, vol. 1, No. 1, 2011, pp. 18-25.

*Primary Examiner* — Cris L. Rodriguez
*Assistant Examiner* — Hao D Mai
(74) *Attorney, Agent, or Firm* — Oblon, McClelland, Maier & Neustadt, L.L.P.

(57) ABSTRACT

An endodontic file system is provided for simultaneously cleaning and shaping multiple root canals, the system includes a drill head having a distal portion and a proximal portion; at least two adjustable couplers on the distal portion of the drill head, each adjustable coupler configured to secure an endodontic file for cleaning a root canal; and a rotary system configured to rotate each adjustable coupler, where at least one endodontic file has an adjustable working distance from the drill head to a root canal of a tooth. In an example, each adjustable coupler can be configured to have a torque control configured to allow for controlling the rotation of the adjustable coupler based on an amount of torque.

18 Claims, 8 Drawing Sheets

(56) References Cited

U.S. PATENT DOCUMENTS

| | | | | | |
|---|---|---|---|---|---|
| 5,534,005 | A | * | 7/1996 | Tokish, Jr. | A61B 17/17 606/79 |
| 5,543,695 | A | * | 8/1996 | Culp | A61C 1/0015 318/432 |
| 5,947,729 | A | * | 9/1999 | Bell | A61C 1/0015 433/27 |
| 5,980,248 | A | * | 11/1999 | Kusakabe | A61C 1/0007 433/131 |
| 6,017,354 | A | * | 1/2000 | Culp | A61B 17/1626 604/22 |
| 6,106,290 | A | * | 8/2000 | Weissman | A61C 1/148 433/118 |
| 6,213,771 | B1 | * | 4/2001 | Fischer | A61C 5/42 433/102 |
| 6,520,773 | B1 | * | 2/2003 | Weber | A61C 5/42 433/27 |
| 6,616,446 | B1 | * | 9/2003 | Schmid | A61B 17/14 433/131 |
| 6,971,878 | B2 | | 12/2005 | Pond | |
| 7,686,614 | B2 | | 3/2010 | Korytkowski | |
| 8,002,544 | B2 | | 8/2011 | Rizoiu et al. | |
| 8,795,279 | B2 | * | 8/2014 | Winslow | A61B 17/1624 606/80 |
| 8,795,280 | B2 | * | 8/2014 | Winslow | A61B 17/1624 606/80 |
| 9,763,680 | B2 | * | 9/2017 | Fritzinger | A61B 17/1615 |
| 2002/0064756 | A1 | * | 5/2002 | Pagnini | A61C 1/003 433/102 |
| 2004/0146830 | A1 | * | 7/2004 | Weinstein | A61B 5/103 433/76 |
| 2004/0146832 | A1 | | 7/2004 | Lampert | |
| 2004/0238223 | A1 | * | 12/2004 | Brady | E21B 17/03 175/320 |
| 2005/0042572 | A1 | * | 2/2005 | Katsuda | A61C 1/0015 433/98 |
| 2010/0330528 | A1 | * | 12/2010 | Hof | A61C 1/185 433/105 |
| 2011/0300506 | A1 | * | 12/2011 | Curry | A61C 5/44 433/75 |
| 2013/0099710 | A1 | * | 4/2013 | Okamoto | A61C 1/0015 318/434 |
| 2014/0255114 | A1 | * | 9/2014 | Diamond | B23B 39/18 408/16 |
| 2014/0342301 | A1 | * | 11/2014 | Fleer | A61C 5/025 433/27 |
| 2017/0281312 | A1 | * | 10/2017 | Khakpour | A61C 5/46 |

* cited by examiner

ENDODONTIC FILE SYSTEM FOR CLEANING AND SHAPING A ROOT CANAL

BACKGROUND

Dental professionals use powered dental handpieces including a rotary endodontic file for a number of different dental procedures. A root canal procedure involves mechanically cleaning and chemically disinfecting multiple root canals of a tooth. Depending on the tooth, there may be two or more root canals that require cleaning and disinfecting. Each root canal can have a different depth which requires an appropriate endodontic file length. Commercially available rotary file systems for mechanically cleaning the root canal are configured to only use a single endodontic file.

SUMMARY

An endodontic file system is provided for simultaneously cleaning and shaping multiple root canals, the system includes a drill head having a distal portion and a proximal portion; at least two adjustable couplers on the distal portion of the drill head, each adjustable coupler configured to secure an endodontic file for cleaning a root canal; and a rotary system configured to rotate each adjustable coupler, where at least one endodontic file has an adjustable working distance from the drill head to a root canal of a tooth. In an example, each adjustable coupler can be configured to have a torque control configured to allow for controlling the rotation of the adjustable coupler based on an amount of torque.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Referring now to the drawings, wherein like reference numerals designate identical or corresponding parts throughout the several views.

Figure 1A:
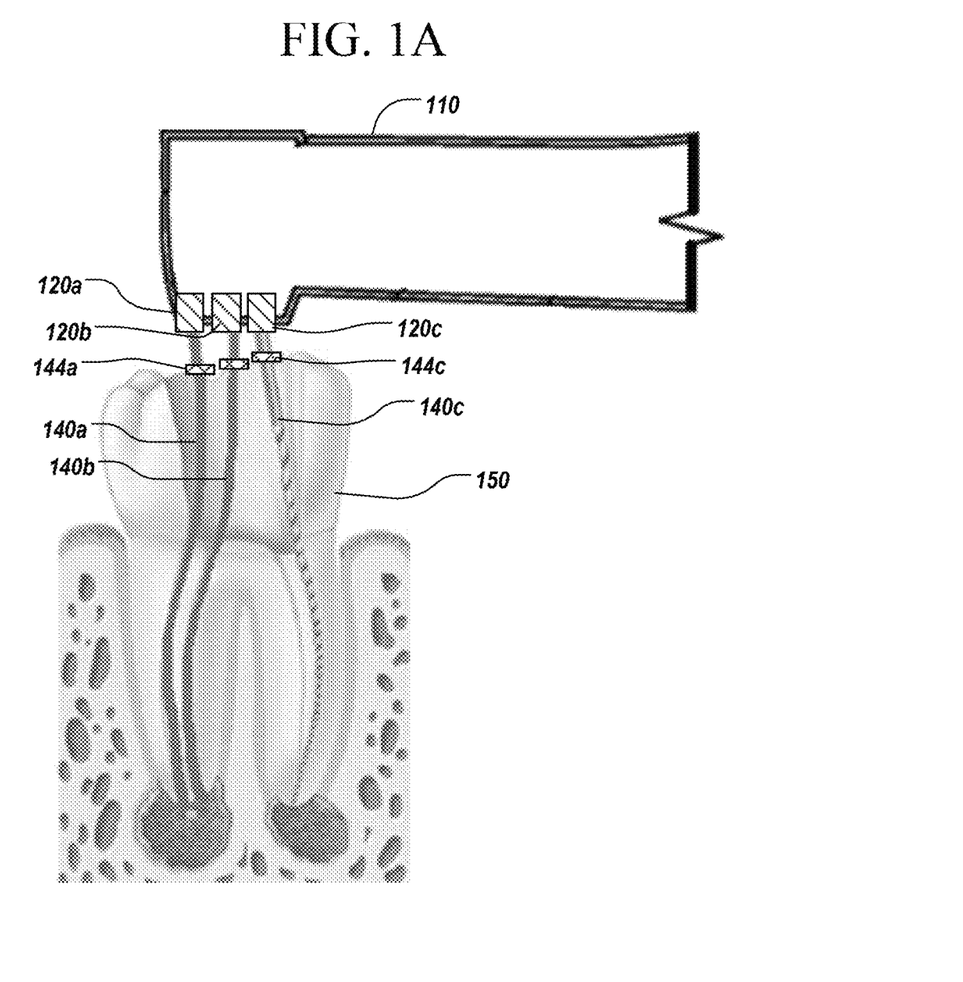
FIG. 1A is a cross-section view of an endodontic file system having a drill head, a set of adjustable couplers, with each adjustable coupler securing an endodontic file that is in a root canal of a tooth according to an example.
Figure 1B:
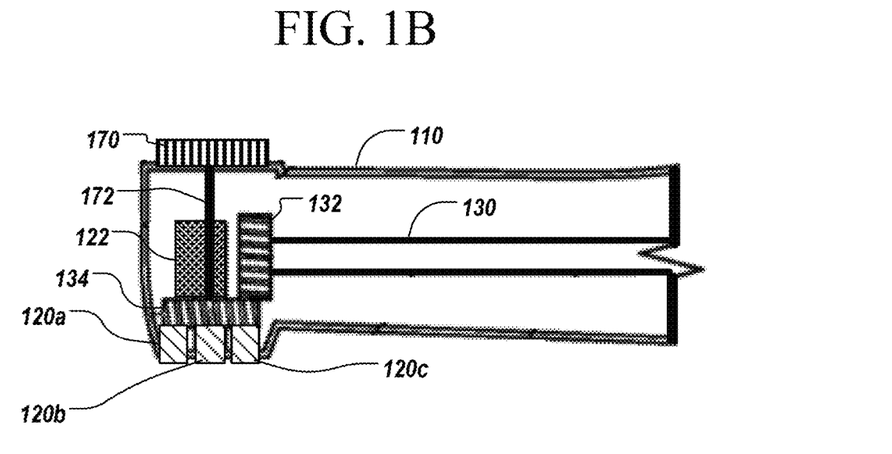
FIG. 1B is a cross-section view of the endodontic file system including a rotary system configured to rotate the set of adjustable couplers according to an example.

FIGS. 1A-1B show a cross-section view of an endodontic file system for simultaneously cleaning and shaping multiple root canals. The endodontic file system includes a drill head 110 having a distal portion and a proximal portion, at least one adjustable coupler 120 on a distal portion of the drill head 110, each adjustable coupler configured to receive and secure an endodontic file 140a-c. The system further includes a rotary system 130 configured to rotate each adjustable coupler 120, where each endodontic file 140a-c is configured to have a working distance 210a-c (see FIGS. 2A-2C) from the drill head 110 to a root canal of a tooth 150.

In an example, a file working distance 212a (see FIG. 2A) can be set using a stopper 144a-c. It is well known that a desired working length of an endodontic file can be established by means of a stopper, usually in the form of a resilient rubber washer, mounted frictionally on the endodontic file for adjustment along the length thereof to a desired position as determined from radiographs of the tooth. In an example, when a stopper 144a-c reaches the desired working length (i.e. reaches a tooth), a torque rotation is modified in at least one of the rotary system 130 and the adjustable coupler 120a-c.

Figure 2A:
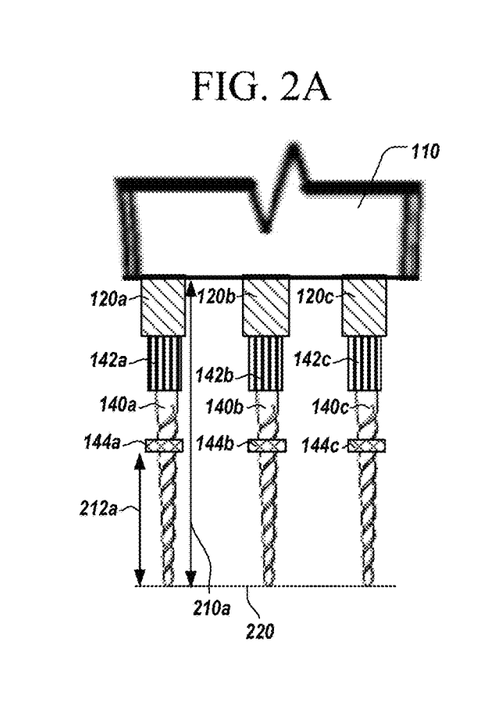
FIG. 2A is a cross-section view of the endodontic file system including a set of endodontic files having a uniform working length according to an example.
Figure 2B:
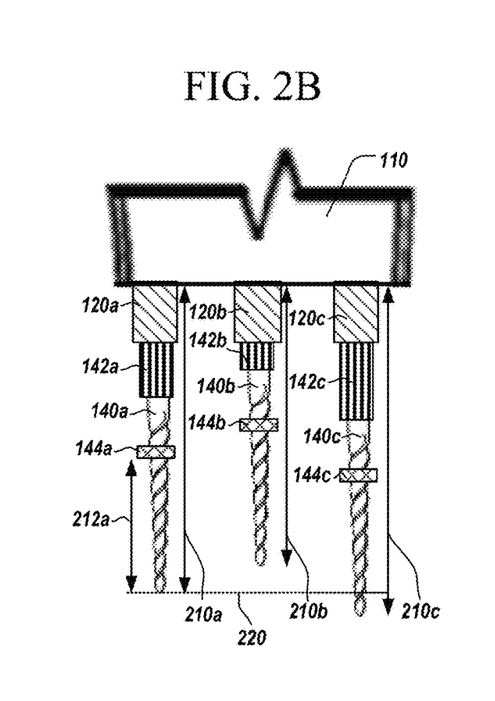
FIG. 2B is a cross-section view of the endodontic file system including an adjustable coupler configured to modify a working distance of an endodontic file to a root canal of the tooth by retracting or extending the endodontic file within the adjustable coupler according to an example.
Figure 2C:
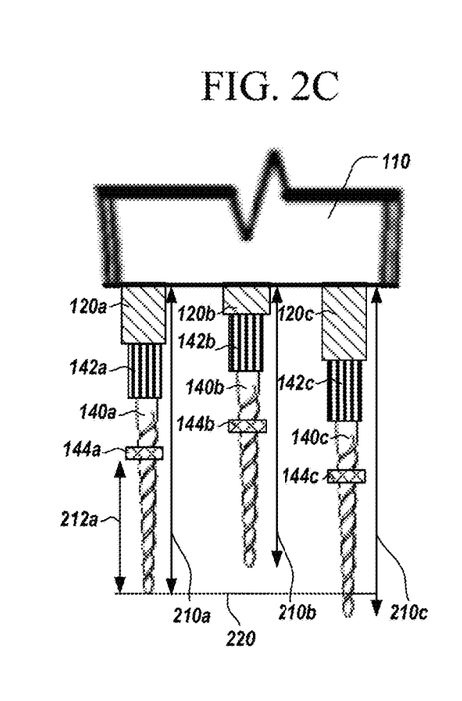
FIG. 2C is a cross-section view of the endodontic file system including an adjustable coupler configured to modify a working distance of an endodontic file to a root canal of the tooth by retracting or extending the adjustable coupler from the drill head according to an example.

In an aspect, the stopper 144a-c can be positioned on each endodontic file 140a-c at a predetermined position in coordination with the working distance 210a-c. In an aspect, the modification of the working distance 210a-c by the adjustable couplers 120a-c has a finer amount of resolution and control than manual placement of the stopper 144a-c.

In an example, the rotary system 130 is configured to rotate a main gear 132 that is configured to rotate a coupler gear 134 that is configured to rotate the one or more adjustable couplers 120a-c and respective endodontic files 140a-c. In an example, the drill head 110 can be configured to work with existing dental drill systems for powering the rotary system 130 such as an air turbine powered by compressed air (not shown).

In an example, the endodontic file system can optionally include an electrical system 122 (See FIG. 1B) configured to provide feedback to a dentist operating the drill. In an example, the electrical system 122 can include one or more sensors (not shown), configured to detect a torque rotation of the one or more adjustable couplers 120a-c, as well as other commonly known components (not shown for simplicity) such as a processor with associated circuitry and power sources. In an example, a pressure sensor can be configured to determine when a stopper 144a-c is reached. In an example, the electrical system 122 can be configured to be powered directly by the rotary system 130 or indirectly by an energy harvester (not shown) from vibrations resulting from operation of the endodontic file system.

In an example, each adjustable coupler 120 can have a securing feature such as a collet or an elastomeric grip (not shown) to secure the endodontic file 140. In an example, the adjustable coupler 120 can have a shape to mate the endodontic file 140.

Figure 1C:
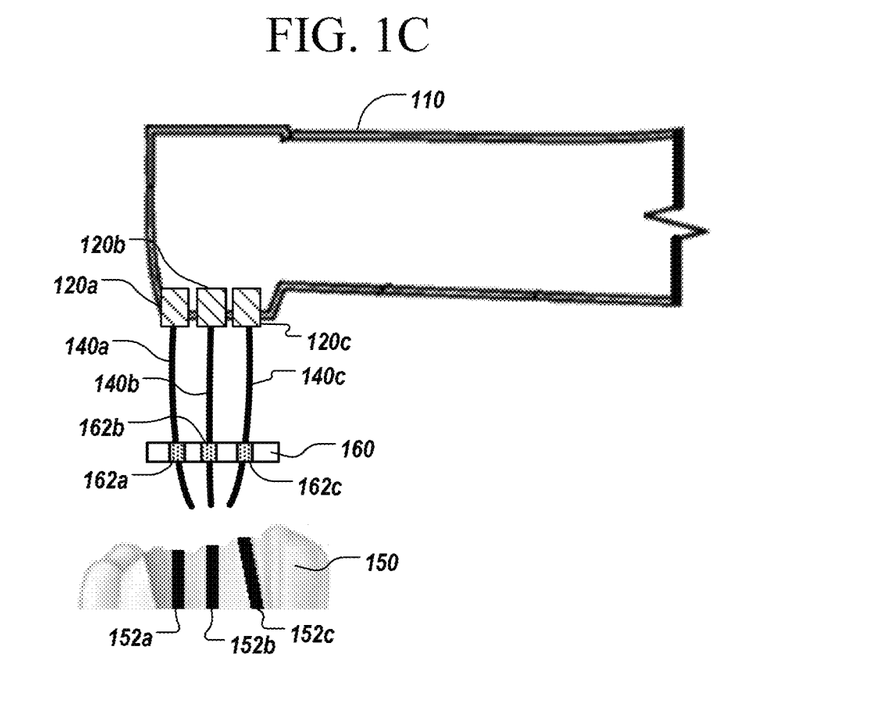
FIG. 1C is a cross-section view of the endodontic file system of FIG. 1A including an alignment guide configured to align a set of endodontic files to a set of root canals of the tooth according to an example.
Figure 1D:
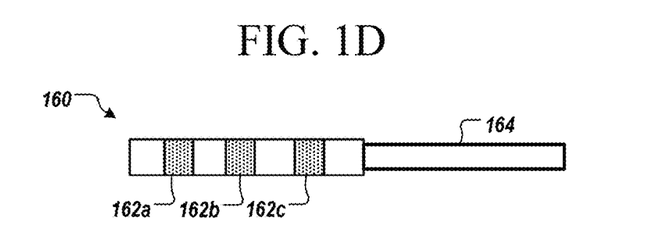
FIG. 1D shows a cross section view of the alignment guide including a handle and a set of openings configured to align a set of endodontic files to a set of root canals of the tooth according to an example.

FIG. 1C shows a cross-section view of the endodontic file system of FIG. 1A including an alignment guide 160 having a set of openings 162a-c configured to align a set of endodontic files 140a-c to a set of root canals 152a-c of the tooth according to an example.

The endodontic file 140 is typically made from flexible shape memory materials such as Ni—Ti. This flexibility is configured to allow for matching a curvature of the root canal. In an example, the set of endodontic files 140a-c can be directed through the set of openings 162a-c of the alignment guide 160 in order to align each endodontic file 140a-c to a respective root canal. Once the alignment is complete, the alignment guide 160 can be removed for unobstructed view of the tooth.

Figure 1E:
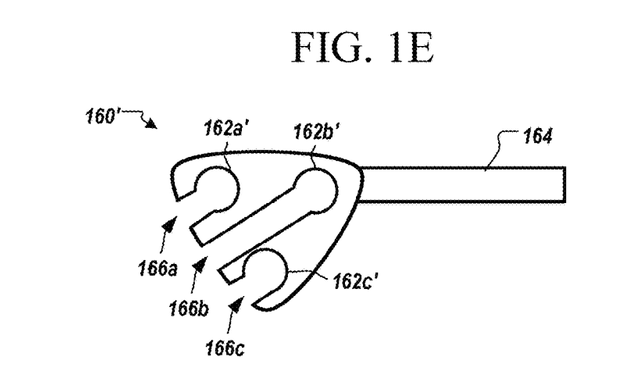
FIG. 1E shows a top view of an alignment guide including a set of openings where each opening has a removal channel according to an example.
Figure 1F:
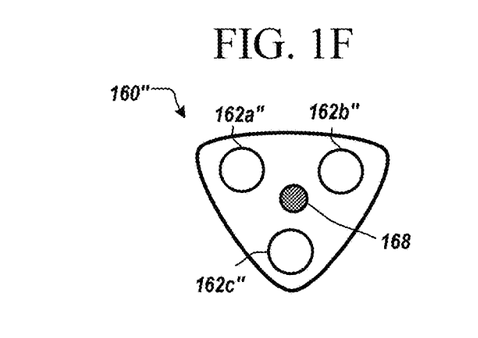
FIG. 1F shows a top view of an alignment guide including a spring according to an example.
Figure 1G:
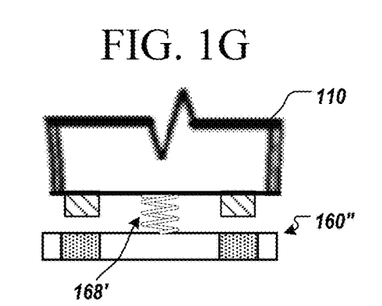
FIG. 1G shows a side view of the drill head connected to the alignment guide by the spring, where the spring is compacted according to an example.
Figure 1H:
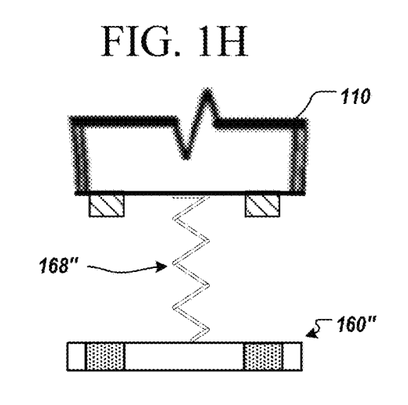
FIG. 1H shows a side view of the drill head connected to the alignment guide by the spring, where the spring is elongated according to an example.

In an example, an alignment guide 160' can include a handle 164 and a set of openings 162'a-c where each opening has a removal channel 166a-c according to an example (See FIG. 1E). In an example, the alignment guide 160' can be used to align the set of endodontic files 140a-c and then be removed out of way for the root canal procedure. In an alternate example, an alignment guide 160" can include a spring 168 and a set of openings 162"a-c where each opening is closed according to an example (See FIG. 1F). As shown in FIGS. 1G-H, the spring 168 can be configured to be attached to the drill head 110 and elongate (elongated spring 168") and recoil (recoiled spring 168'). In an example, the alignment guide 160" can be used to align the set of endodontic files 140a-c and then be recoiled out of way for the root canal procedure.

Drill Head

Figure 3A:
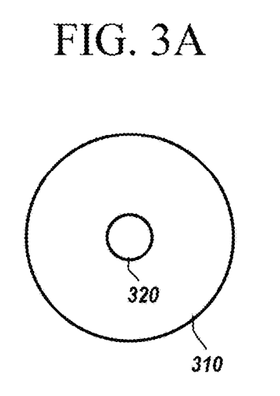
FIG. 3A is a drawing of a drill head having a circular shape and an adjustable coupler according to an example.
Figure 3B:
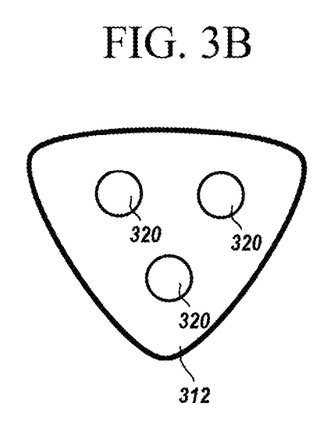
FIG. 3B is a drawing of a drill head having a triangular shape and a set of adjustable couplers according to an example.
Figure 3C:
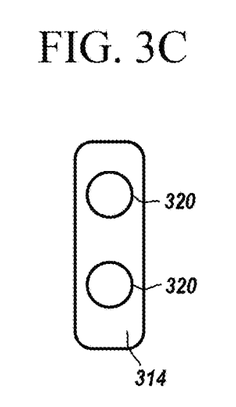
FIG. 3C is a drawing of a drill head having a rectangular shape and a set of adjustable couplers according to an example.

In some implementations, the drill head 110 can have different spatial configurations based on a set of adjustable couplers 120a-c. As shown in FIGS. 3A-C, a drill head 310 can have a circular shape 310, a drill head 312 can have a triangular shape 312, and a drill head 314 can have rectangular shape. In an example, the drill head 312 can be used for upper molar teeth that have three root canals. In an example, the drill head 314 can be used for the upper first pre-molar teeth that usually have two root canals. In all other aspects, the drill heads 310, 312, 314 are the same as the drill head 110.

In an example, the alignment guide 160 can be configured to have a set of openings 162a-c matching the spatial configuration of the set of adjustable couplers 120a-c on the drill heads 310, 312, 314.

Figure 3D:
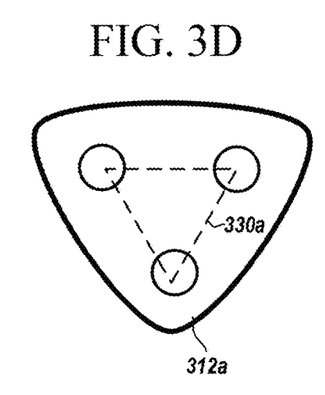
FIG. 3D is a drawing of the drill head of FIG. 3B having a first spatial arrangement of the set of adjustable couplers according to an example.
Figure 3E:
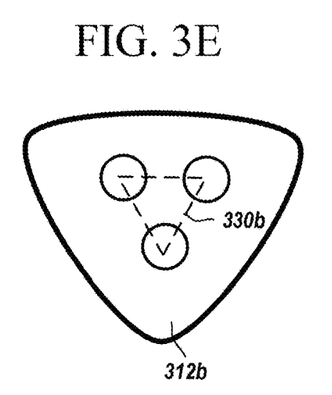
FIG. 3E is a drawing of the drill head of FIG. 3B having a second spatial arrangement of the set of adjustable couplers according to an example.

In some implementations, the set of adjustable couplers 120a-c can be configured to be spatially adjustable on the drill head 110. As shown in FIGS. 3D-E, the drill head 312a-b can have a first spatial arrangement 330a of the set of adjustable couplers 120a-c and an adjusted spatial arrangement 330b according to an example. In an aspect, the adjusted spatial arrangement can be configured to reduce the torque rotation from any one of the one or more adjustable couplers 120a-c.

Adjustable Coupler

In some implementations, each adjustable coupler 120 can be configured to be adjustable in several ways. In an example, the adjustable coupler 120 can be configured to have an adjustable working distance 210a-c relative to the drill head 110. The set of adjustable couplers 120a-c can have uniform working lengths 210a (See 220 in FIG. 2A) and varying working lengths 210a-c (See FIG. 2B) from the drill head 110 relative to at least one root canal of the tooth 150.

In an example, the adjustable coupler 120 can be adjusted within the drill head 110 manually by rotating a thumb knob 170 on the drill head 110. In an example, the thumb knob 170 can have an arm 172 that is configured to modify a position of the coupler gear 134. In an example, the thumb knob 170 can be configured to control the electrical system 122 to control an electric motor (not shown) to modify a position of the adjustable coupler 120 within the drill head 110 by extending the adjustable coupler 120 out of the drill head 110 or retracting the adjustable coupler 120 within the drill head 110. In an aspect, modification of the position of the adjustable coupler 120 can have a fine resolution.

Torque Control

In an example, each adjustable coupler 120 can be configured to have a torque control (not shown) configured to allow for controlling the rotation of the adjustable coupler 120 based on an amount of torque. Examples of torque control include a slip clutch, a ball detent type limiter, a synchronous magnetic torque limiter, and a friction plate clutch. In an example, the torque control of each adjustable coupler 120 can be independent from another adjustable coupler. In an aspect, the torque control can be configured to prevent damaging torsion in the canal by the endodontic file 140a-c when the endodontic file 140a-c is applying stress in excess of a torsion threshold. U.S. Pat. No. 4,536,156 incorporated herein by reference in its entirety describes an example of a slip clutch that can be used in a dental drill.

In an example, the torque control can be configured to detect the modified torque rotation that occurs when a stopper 144a-c on an endodontic file 140a-c is reached, to stop rotation of the respective adjustable coupler 120, and to adjust another adjustable coupler 120 in order to allow another endodontic file 140 to continue filing. For example, when a stopper 144b is detected, a stopping distance for a respective endodontic file 140b secured in a respective adjustable coupler 120b is reached. The torque control can be configured to stop the rotation of the adjustable coupler 120b as well as at least one of: to retract the adjustable coupler 120b into the drill head 110 (FIG. 2C), to retract the endodontic file 140b into the adjustable coupler 120b (FIG.

2B), to extend another adjustable coupler 120c from the drill head 110 (FIG. 2C), and to extend another endodontic file 140 from the adjustable coupler 120b (not shown).

Figure 4:
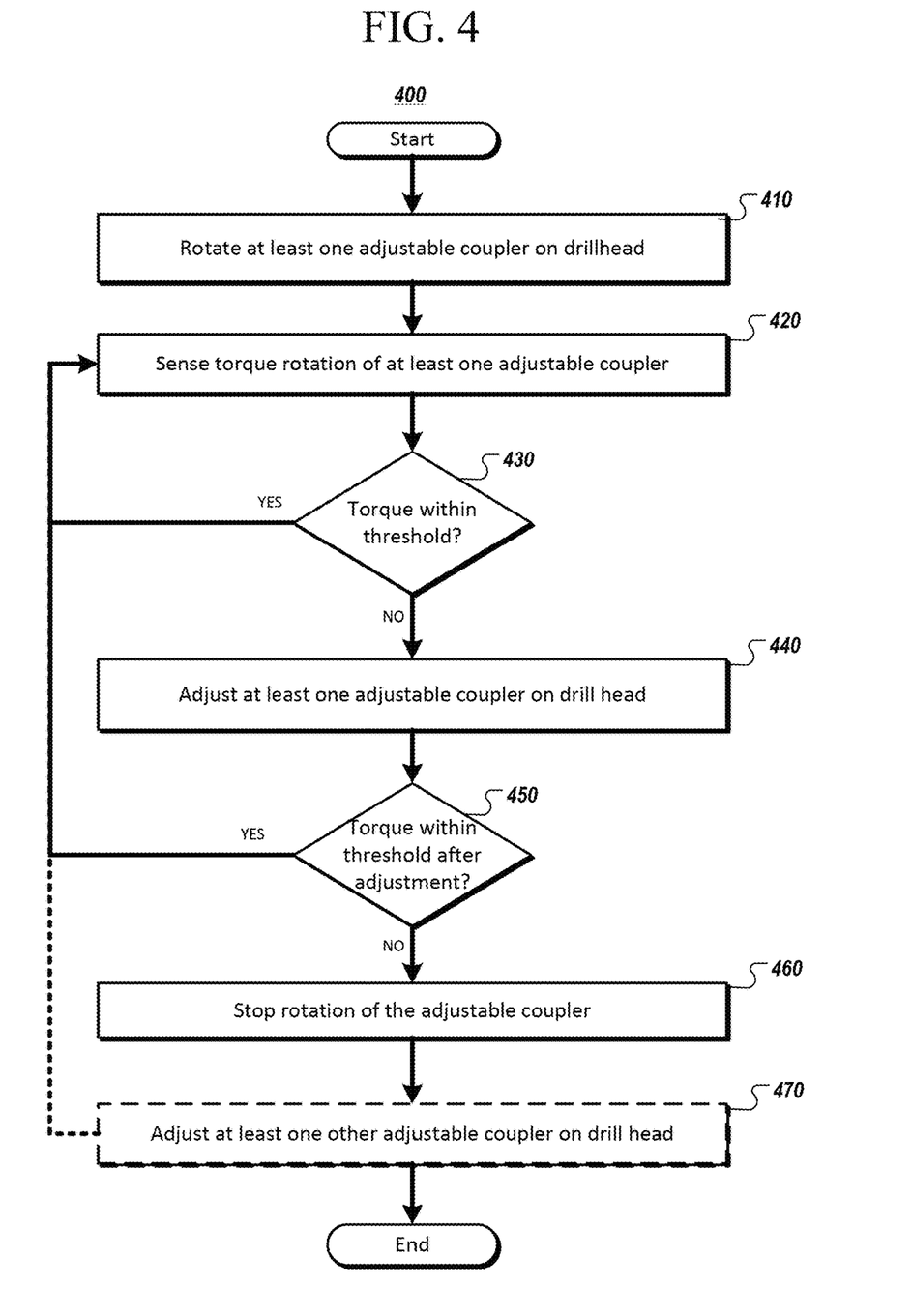
FIG. 4 is a flow chart showing a method for adjusting a torque rotation of the adjustable coupler according to an example.

FIG. 4 is a flow chart showing a method 400 for adjusting a torque rotation of the adjustable coupler 120 according to an example. At step 410, at least one adjustable coupler 120 on a drill head 110 is configured to be rotated. In an example, the rotary system 130 can be configured to rotate a set of adjustable couplers 120a-c in parallel. In an example, the rotary system 130 can be configured to rotate each adjustable coupler 120 independently.

At step 420, a torque rotation of at least one adjustable coupler 120 is sensed. In an example, the torque rotation can be sensed by the rotary system. In an example, the torque rotation can be sensed by a sensor on the adjustable coupler 120 (not shown).

At step 430, a comparison is made between the sensed torque rotation and a torque threshold. In an example, the electrical system 122 is used to make the comparison. Alternatively, the torque control can be purely mechanical. When the sensed torque rotation is greater than the torque threshold, the method advances to step 440. When the sensed torque rotation is less than or equal to the torque threshold, the method returns to step 420.

At step 440, a position of at least one adjustable coupler 120 is configured to be adjusted on the drill head 110. FIG. 5B, described below, shows different examples of adjusting the adjustable coupler 120 according to different embodiments described herein.

At step 450, a comparison is made, with the adjusted position, a between the sensed torque rotation and a torque threshold. In an example, the electrical system 122 can be configured to sense the torque rotation. When the sensed torque rotation is greater than the torque threshold, the method advances to step 460. When the sensed torque rotation is less than or equal to the torque threshold, the method returns to step 420.

At step 460, the rotation of the adjustable coupler 120 is stopped. Optionally, at step 270 a position of at least one other adjustable coupler 120 can be configured to be adjusted on the drill head 110. For example, when the rotation of the adjustable coupler 120 is stopped due to the torque control detecting a stopper 144a-c, another adjustable coupler 120 can be adjusted in order to allow another endodontic file 140 to continue filing.

Assembly Method

Figure 5A:
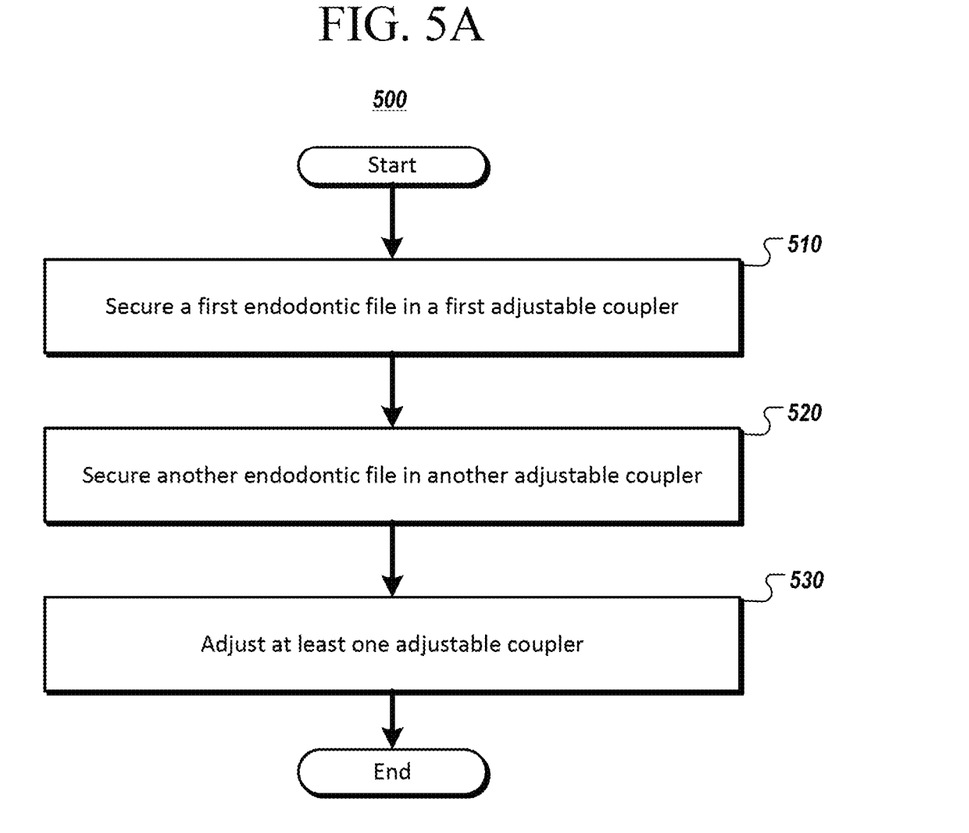
FIG. 5A is a flow chart showing a method for assembling an endodontic file system for simultaneously cleaning and shaping multiple root canals according to an example.
Figure 5B:
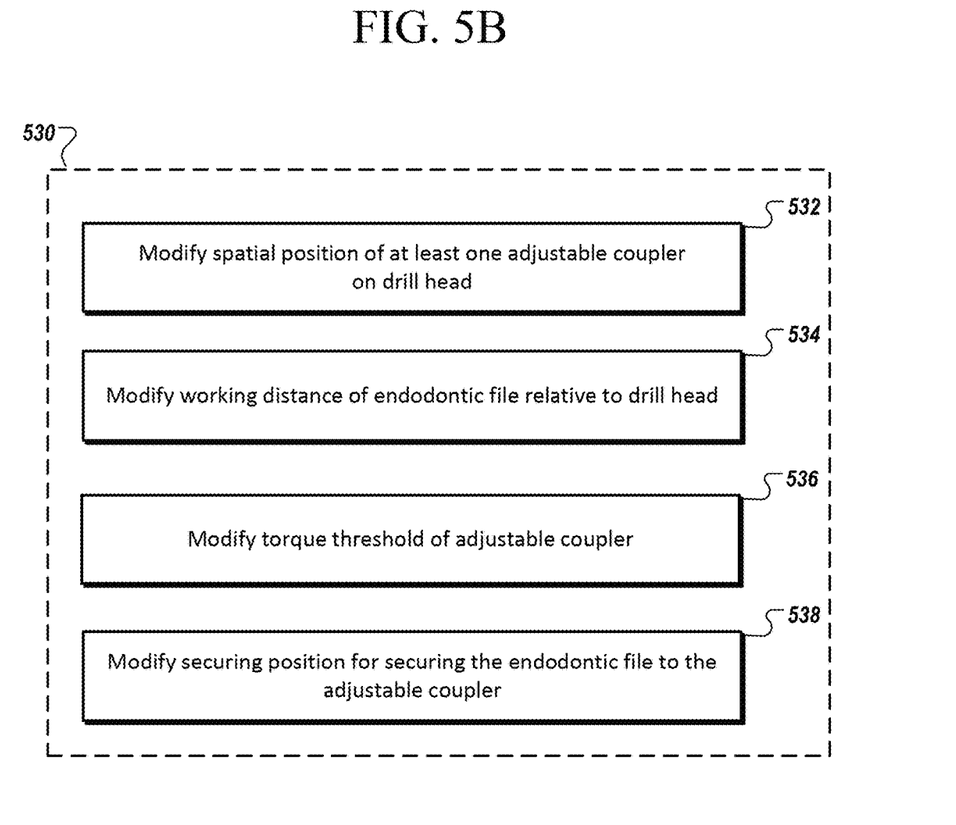
FIG. 5B shows different examples of adjusting the adjustable coupler according to different embodiments described herein.

FIG. 5A shows a flow chart of a method 500 for assembling an endodontic file system for simultaneously cleaning and shaping multiple root canals according to an example. At step 510, a first endodontic file 140a is secured in a first adjustable coupler 120 on a drill head 110. In an example, each endodontic file 140a-c can be secured in the adjustable coupler 120 in ways currently available such as a collet and an elastomeric grip. At step 520, a second endodontic file 140b is secured in a second adjustable coupler 120 on the drill head 110. At step 530, at least one adjustable coupler 120 is adjusted on the drill head 110.

FIG. 5B shows different examples of adjusting the adjustable coupler 120 according to different embodiments described herein. In an example, the adjustable coupler 120 is adjusted on the drill head 110 by modifying a spatial position of at least one adjustable coupler 120 on the drill head 110 (532). In an example, the adjustable coupler 120 is adjusted on the drill head 110 by modifying a working distance of the endodontic file 140a-c relative to drill head 110 (534). In an example, the adjustable coupler 120 is adjusted on the drill head 110 by modifying a torque threshold of the adjustable coupler 120 (536). In an example, the adjustable coupler 120 is adjusted on the drill head 110 by modifying a securing position for securing the endodontic file 140 to the adjustable coupler 120 (538).

In an aspect, an advantage of using this endodontic file system is requiring less irrigants during the root canal treatment. An irrigant is an anti-microbial agent that is used in cleaning the root canals. In a root canal procedure, chemical cleaning with an irrigant is done simultaneously as mechanical cleaning with the endodontic file 140a-c. With existing single file drills, for each canal an irrigant solution is applied in the single root canal. With two or more canals prepared at once, the irrigant solution can be applied to the two or more canals simultaneously.

In an aspect, an advantage of using this endodontic file system is resulting in a faster procedure. By simultaneously cleaning with a set of endodontic files 140a-c, a total time for the root canal procedure can be reduced.

In an aspect, an advantage of using this endodontic file system is reduced total pressure on a wrist of a dentist performing the cleaning. In an example, by simultaneously cleaning with a set of endodontic files 140a-c, a total pressure applied is distributed among the set of root canals. In an example, by simultaneously cleaning with a set of endodontic files 140a-c, a reduced amount of time applying pressure by the dentist performing the cleaning is achieved.

Obviously, numerous modifications and variations of the present disclosure are possible in light of the above teachings. It is therefore to be understood that within the scope of the appended claims, the invention may be practiced otherwise than as specifically described herein.

The invention claimed is:

1. An endodontic file system for simultaneously cleaning and shaping multiple root canals, the system comprising:
   a drill head having a distal portion and a proximal portion;
   a plurality of endodontic files for cleaning and shaping at least one root canal of a tooth, having a proximal end and a distal end;
   a plurality of adjustable couplers disposed within the distal portion of the drill head, each of the plurality of adjustable couplers being configured to secure a corresponding one of the plurality of endodontic files; and
   a rotary device configured to rotate the plurality of adjustable couplers,
   wherein an axial position of each of the plurality of adjustable couplers within the drill head is adjustable,
   wherein each of the plurality of adjustable couplers is configured to adjust a working distance of the corresponding one of the plurality of endodontic files, the working distance being a distance from a surface of the drill head to the distal end of the corresponding one of the plurality of endodontic files.

2. The endodontic file system of claim 1, wherein each of the plurality of adjustable couplers is configured to be adjustable by modifying a spatial position of each of the plurality of adjustable couplers disposed within the drill head.

3. The endodontic file system of claim 1, wherein the corresponding one of the plurality of endodontic files is configured to be adjusted by modifying a securing position of the corresponding one of the plurality of endodontic files within a respective one of the plurality of adjustable couplers.

4. The endodontic file system of claim 1, wherein each of the plurality of adjustable couplers is configured to adjust the working distance of the corresponding one of the plurality of endodontic files relative to a depth of a respective one of the at least one root canal of the tooth.

5. The endodontic file system of claim 1, further comprising:
a torque control configured to detect a rotation of each of the plurality of adjustable couplers,
wherein the torque control is configured to modify the rotation of each of the plurality of adjustable couplers based on a comparison of the detected rotation and a pre-determined torque threshold.

6. The endodontic file system of claim 5, wherein each of the plurality of adjustable couplers is configured to be independently adjusted by modifying the pre-determined torque threshold.

7. The endodontic file system of claim 1, further comprising:
an alignment guide having a set of openings configured to align each of the plurality of endodontic files to a respective root canal of the tooth.

8. The endodontic file system of claim 1, wherein each of the plurality of adjustable couplers is configured to be arranged on the drill head corresponding to a spacing of the at least one root canal of the tooth.

9. The endodontic file system of claim 1, wherein one or more of the plurality of endodontic files includes a stopper configured to set a file working distance, the file working distance being a distance from the stopper to the distal end of a respective one of the one or more of the plurality of endodontic files,
wherein the file working distance of at least one of the one or more of the plurality of endodontic files is pre-determined relative to a depth of the at least one root canal of the tooth,
wherein, when an active working distance, the active working distance being a depth of the distal end of each of the plurality of endodontic files within a corresponding one of the at least one root canal of the tooth, reaches the file working distance for a first one of the plurality of endodontic files, each of the plurality of adjustable couplers is configured to adjust the working distance to allow a subsequent one or more of the plurality of endodontic files to continue cleaning and shaping a respective one or more of the at least one root canal of the tooth.

10. A method for simultaneous cleaning and shaping of multiple root canals, the method comprising:
outfitting a drill head, the drill head having a distal portion and a proximal portion;
shaping, by a corresponding at least one endodontic file, at least one root canal of a tooth, the corresponding at least one endodontic file being secured by at least one adjustable coupler disposed within the distal portion of the drill head, the at least one adjustable coupler being rotated by a rotary device configured to rotate the at least one adjustable coupler;
measuring, via processing circuitry, a torque value of each of the at least one adjustable coupler; and
deactivating, via the processing circuitry, one or more of the at least one adjustable coupler based upon the measuring of the torque value of each of the at least one adjustable coupler,
wherein the outfitting includes installing at least one endodontic file for shaping the at least one root canal of the tooth in a pre-determined arrangement, each of the at least one endodontic file having a proximal end and a distal end,
wherein the installing includes coupling one of the at least one endodontic file to a corresponding one of the at least one adjustable coupler disposed within the distal portion of the drill head,
wherein an axial position of each of the at least one adjustable coupler within the drill head is adjustable,
wherein each of the at least one adjustable coupler is configured to adjust a working distance of a corresponding one of the at least one endodontic file, the working distance being a distance from a surface of the drill head to the distal end of the corresponding one of the at least one endodontic file.

11. The method of claim 10, wherein each of the at least one adjustable coupler is configured to be adjustable by modifying a spatial position of each of the at least one adjustable coupler disposed within the drill head.

12. The method of claim 10, wherein the corresponding one of the at least one endodontic file is configured to be adjusted by modifying a securing position of the corresponding one of the at least one endodontic file within a respective one of the at least one adjustable coupler.

13. The method of claim 10, wherein each of the at least one adjustable coupler is configured to adjust the working distance of the corresponding one of the at least one endodontic file relative to a depth of a respective one of the at least one root canal of the tooth.

14. The method of claim 10, wherein the deactivating, via the processing circuitry, the one or more of the at least one adjustable coupler based upon the measuring of the torque value of each of the at least one adjustable coupler further comprises a comparison of the measured torque value to a pre-determined torque threshold, wherein a torque control is configured to modify the rotation of each of the at least one adjustable coupler based on the comparison.

15. The method of claim 14, wherein each of the at least one adjustable coupler is configured to be independently adjusted by modifying the pre-determined torque threshold.

16. The method of claim 10, further comprising aligning each of the at least one endodontic file with a corresponding one of the at least one root canal of the tooth, wherein the aligning is aided by an alignment guide having a set of openings corresponding to the corresponding one of the at least one root canal of the tooth.

17. The method of claim 10, wherein each of the at least one adjustable coupler is configured to be arranged on the drill head corresponding to a spacing of the at least one root canal of the tooth.

18. The method of claim 10, further comprising adjusting the working distance of one or more of the at least one endodontic file based upon a comparison of an active working distance and a file working distance,
wherein the active working distance is a depth of the distal end of each of the at least one endodontic files within a corresponding one of the at least one root canal of the tooth,
wherein the file working distance of each of the at least one endodontic file is determined by a distance between a stopper and the distal end of a respective one of the one or more of the at least one endodontic file, the file working distance being pre-determined relative to a depth of the corresponding one of the at least one root canal of the tooth,
wherein the working distance of the one or more of the at least one endodontic file is adjusted when the active working distance reaches the file working distance, allowing a subsequent one or more of the at least one endodontic file to continue shaping a respective one or more of the at least one root canal of the tooth.

\* \* \* \* \*